US008579791B2

(12) United States Patent
Whisenant et al.

(10) Patent No.: US 8,579,791 B2
(45) Date of Patent: Nov. 12, 2013

(54) VENTRICULAR ASSIST DEVICE AND RELATED METHODS

(75) Inventors: Brian K. Whisenant, Salt Lake City, UT (US); Scott D. Miles, Sandy, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 0 days.

(21) Appl. No.: 13/567,824

(22) Filed: Aug. 6, 2012

(65) Prior Publication Data

US 2013/0030454 A1 Jan. 31, 2013

Related U.S. Application Data

(62) Division of application No. 12/436,056, filed on May 5, 2009, now Pat. No. 8,235,885.

(60) Provisional application No. 61/050,568, filed on May 5, 2008.

(51) Int. Cl.
*A61N 1/362* (2006.01)

(52) U.S. Cl.
USPC ............................................................ 600/16

(58) Field of Classification Search
USPC ............................................................ 600/16
See application file for complete search history.

(56) References Cited

U.S. PATENT DOCUMENTS

| | | | |
|---|---|---|---|
| 5,190,528 A | 3/1993 | Fonger et al. | |
| 5,928,132 A | 7/1999 | Leschinsky | |
| 6,090,096 A | 7/2000 | St. Goar et al. | |
| 6,306,116 B1 | 10/2001 | Hancock | |
| 6,344,022 B1 | 2/2002 | Jarvik | |
| 6,974,436 B1 | 12/2005 | Aboul-Hosn et al. | |
| 2001/0027287 A1 | 10/2001 | Shmulewitz et al. | |
| 2003/0176760 A1 | 9/2003 | El Oakley et al. | |
| 2004/0102674 A1 | 5/2004 | Zadini et al. | |
| 2004/0191116 A1 | 9/2004 | Jarvik et al. | |
| 2004/0249431 A1 | 12/2004 | Ransbury et al. | |
| 2005/0165344 A1 | 7/2005 | Dobak, III | |
| 2005/0187425 A1 | 8/2005 | Alferness et al. | |
| 2005/0251187 A1 | 11/2005 | Beane et al. | |

(Continued)

FOREIGN PATENT DOCUMENTS

| | | |
|---|---|---|
| WO | WO 00/37139 | 6/2000 |
| WO | WO 2005/037345 | 4/2005 |
| WO | WO 2007/047212 | 4/2007 |
| WO | WO 2008/027869 | 3/2008 |

*Primary Examiner* — Christopher D Koharski
*Assistant Examiner* — Philip Edwards
(74) *Attorney, Agent, or Firm* — David L. Stott (57) ABSTRACT

A method and system are provided for percutaneously gaining access to oxygenated bood with an anastomosis device and pumping such oxygenated blood to other arterial regions of the vascular system. In one embodiment, a system may include an anastomosis device extending through an opening of the atrial septum. A filament may be coupled to the anastomosis device. A snare may access the right atrium through the superior vena cava, grasp the filament, and withdraw the filament through the superior vena cava. The filament may then be used as a guide to direct a catheter, a conduit or some other structure into the right atrium of the heart via the superior vena cava. A flow path may be defined between the anastomosis device and an arterial location, such as in the aorta, such that at least some oxygenated blood may by-pass the left ventricle and be discharged into the aorta.

16 Claims, 13 Drawing Sheets

(56) References Cited

U.S. PATENT DOCUMENTS

| | | |
|---|---|---|
| 2005/0256540 A1 | 11/2005 | Silver et al. |
| 2006/0270893 A1 | 11/2006 | Bolling et al. |
| 2007/0161845 A1 | 7/2007 | Magovern et al. |
| 2007/0293724 A1 | 12/2007 | Saadat et al. |
| 2009/0088597 A1 | 4/2009 | Frazier et al. |
| 2009/0112050 A1* | 4/2009 | Farnan et al. .................. 600/16 |

* cited by examiner

VENTRICULAR ASSIST DEVICE AND RELATED METHODS

CROSS-REFERENCE TO RELATED APPLICATIONS

This application is a divisional of application Ser. No. 12/436,056, filed May 5, 2009, and entitled VENTRICULAR ASSIST DEVICE AND RELATED METHODS, pending, which claims priority of provisional applications Ser. No. 61/050,568, filed May 5, 2008, entitled METHOD AND APPARATUS FOR CONNECTING A VENTRICULAR ASSIST DEVICE TO A HEART, the disclosure of each of which are also incorporated by reference herein in their entireties.

TECHNICAL FIELD

The present invention relates generally to methods, apparatus and systems for connecting a ventricular assist device to a heart, More specifically, the present invention relates to methods and apparatus for percutaneously connecting a ventricular assist device to a heart.

BACKGROUND

There are several instances when it is desirable to provide assistance to the heart in performing its function of pumping blood through the body. For example, when the heart has been arrested to perform a surgical procedure and then started again after the procedure, the heart conventionally needs assistance for some period of time until it has developed sufficient strength and overcome the trauma of being arrested. In other examples, a patient may experience some form of cardiac failure such that the heart requires more permanent assistance.

One type of assist device is known as a ventricular assist device (VAD) which helps pump blood through the body when, for example, a ventricle lacks sufficient strength to perform this function. More specifically, left ventricular assist devices (LVADs) have. been used for some time to assist in the flow of oxygenated blood through the body.

An LVAD may be implemented through a procedure so as to couple, either directly, or indirectly, the device to the left atrium or left ventricle of the heart. Many of such procedures require open-heart surgery and are therefore, extremely invasive and are particularly burdensome on patients that are already experiencing extreme health problems. Other procedures may he performed, and devices implemented, in a less invasive manner, but they may still pose a considerable risk to a patient or may be impractical for longer term use.

As such, it would be advantageous for a less invasive and less life threatening methods for providing an LVAD system or apparatus to a patient experiencing circulatory challenges. Further, in many instances, it would be advantageous for such system, apparatus and method to be implanted for the long-term use and benefit of the patient.

BRIEF SUMMARY OF THE INVENTION

The present invention is directed to methods and systems for percutaneously connecting a ventricular assist device to a heart as well as to components used in such methods and systems.

In accordance with one embodiment of the present invention, a system to assist the left ventricle of a heart is provided. The system includes an anastomosis device coupled to an intra-atrial (or intra-ventricular) septum and providing a flow path between a left atrium and a right atrium of a heart (or from the left ventricle to the right ventricle of a heart). A flow path including at least one conduit is configured to flow oxygenated blood from the left atrium (or left ventricle), through the anastomosis device, through the superior vena cava and back to an artery such as the aorta, a brachial artery, axillary artery, carotid artery, subclavian artery or other artery. A pumping device is coupled with the at least one conduit to help effect the flow of oxygenated blood along the flow path. In one particular embodiment, a filament is coupled with the anastomosis device.

In accordance with another embodiment of the invention, a method for percutaneously connecting a ventricular assist device to a heart is provided. The method includes accessing a right atrium or a right ventricle of the heart with a catheter through an inferior vena cava. The atrial or ventricular septum of the heart is punctured to access oxygenated blood in a left atrium or a left ventricle of the heart and an anastomosis device is implanted in the septum. The catheter is withdrawn from the heart while leaving a filament attached to the anastomosis device, snare device is guided into the heart through the superior vena cava. The filament is grasped or snared with the snare device and pulled back through superior vena cava. A conduit is guided to the anastomosis device through use of the filament. The conduit is coupled to the anastomosis device, oxygenated blood is flowed from the left atrium or left ventricle through the conduit and returned from the conduit to an artery. In one embodiment, access to the superior vena cava may be accomplished through a jugular vein or a subclavian vein. In another embodiment, access to the aorta may be accomplished via a brachial artery, a carotid artery, an axillary artery or a subclavian artery.

In accordance with another embodiment of the invention, a kit is provided for percutaneous connection of a left ventricular assist device to a heart. The kit includes an anastomosis device sized and configured to be installed in an opening of an atrial or ventricular septum. A filament is coupled to the anastomosis device. A snare device is sized and configured to access a right atrium or right ventricle through a superior vena cava, the snare device also being configured to grasp the filament and pull the filament through the superior vena cava.

In accordance with another embodiment of the present invention, a method of guiding a structure to a right atrium or right ventricle of a heart is provided. The method comprises accessing the right atrium or right ventricle through an inferior vena cava and attaching a filament to a wall of the atrium or a wall of the ventricle. The right atrium or right ventricle is accessed with a snare device through the superior vena cava and the filament is grasped with the snare device and withdrawn through the superior vena cava. The structure is then guided through the superior vena cava into the right atrium or right ventricle using the filament.

In accordance with another particular embodiment a method includes accessing a right atrium of the heart with a catheter through the femoral vein and inferior vena cava; puncturing the atrial septum of the heart to access oxygenated blood in a left atrium of the heart; implanting an anastomosis device to the right atrium side of the atrial septum to access blood in the left atrium; withdrawing the catheter from the right atrium and leaving a filament attached to the anastomosis device; accessing the anastomosis device percutaneously through a subclavian or jugular vein at a subclavian or jugular access point; guiding a snare device into right atrium from the subclavian or jugular access point; snaring the filament with the snare device and pulling the filament back through the subclavian or jugular access point; inserting an in-flow catheter of the ventricular assist device to the anastomosis device with the filament as a guide to access the oxygenated blood; and percutaneously attaching an out-flow catheter of the ventricular assist device to, for example, a brachial or carotid artery, via another anastomosis device or another type of inter-connection.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
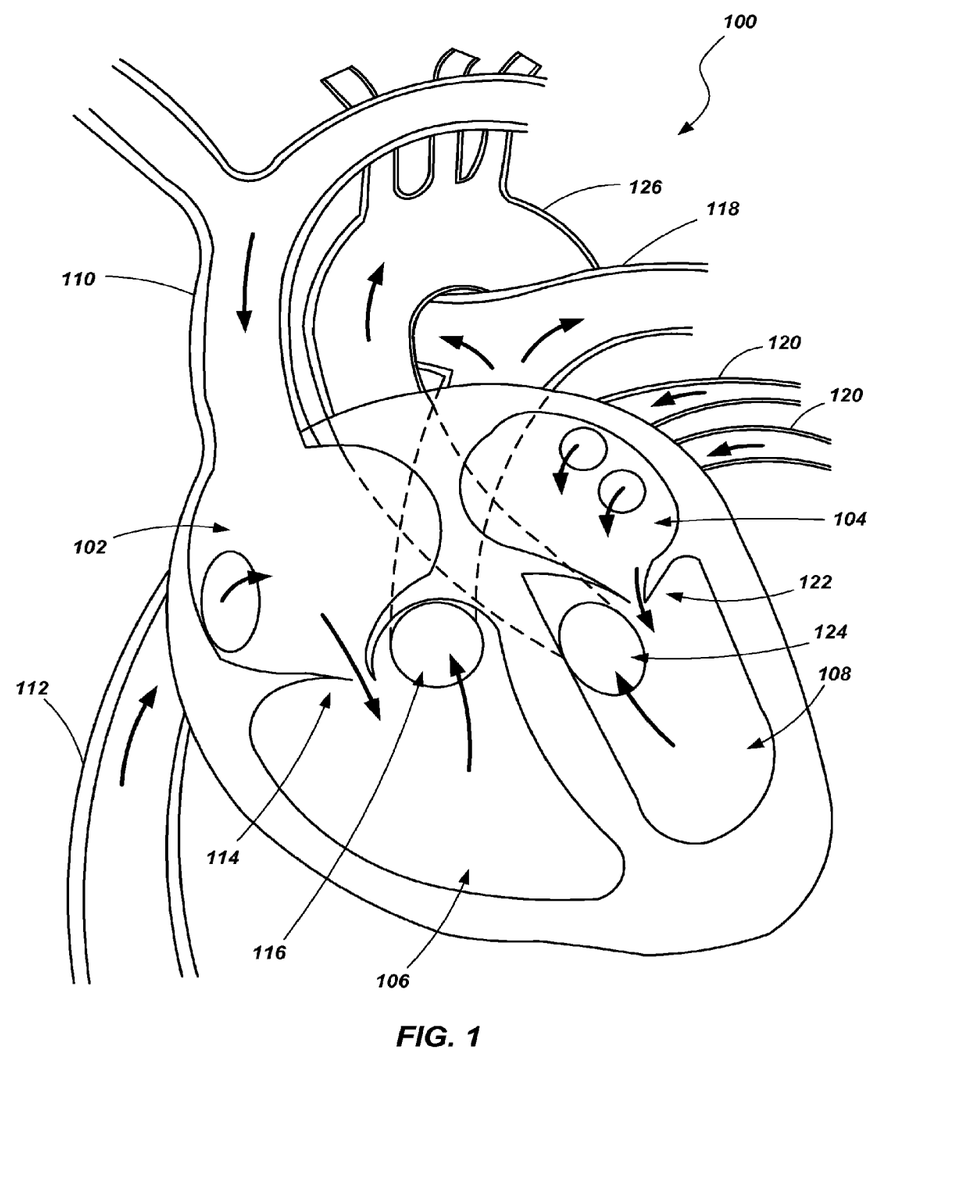
FIG. 1 is a simplified, cross-sectional view of a human heart and certain blood vessels associated therewith.

Embodiments of the present invention are directed to methods, apparatus and systems for percutaneously connecting a ventricular assist device to a heart. Referring first to FIG. 1, a simplified, cross-sectional view of a human heart 100 is shown for purposes of context in describing embodiments of the present invention.

The human heart 100 includes several chambers that effect blood flow through the human body. These chambers include the right atrium 102, the left atrium 104, the right ventricle 106 and the left ventricle 108. The right atrium 102 receives unoxygenated blood from veins including the superior vena cava 110 and the inferior vena cava 112. It will be appreciated by those of ordinary skill in the art that the superior vena cava 110 receives blood from various veins such as the jugular veins, the subclavian veins, and numerous others. Likewise, those of ordinary skill in the art will appreciate that the inferior vena cava 112 receives blood from various veins such as the femoral veins.

Blood passes from the right atrium 102 to the right ventricle 106 through a bicuspid valve 114. Upon contraction of the right ventricle 106, blood is passed through the pulmonary valve 116 and through the pulmonary artery 118 to the lungs (not shown). The lungs oxygenate the blood which then returns to the heart 100, via pulmonary veins 120, to the left atrium 104.

Oxygenated blood passes through the mitral valve 122 and into the left ventricle 108. Upon contraction of the left ventricle 108, oxygenated blood passes through the aortic valve 124 and into the aorta 126. The aorta passes the blood to a network of arteries including the brachiocephalic artery, subclavian arteries, axillary arteries, brachial arteries, the carotid arteries, the femoral arteries and many others as will be appreciated by those of skill in the art.

As noted above, there are various situations where the heart needs some assistance in pumping blood through its network of arteries and veins. One type of assist device is a ventricular assist device (VAD) wherein assistance is provided to one of the ventricles by helping to pump the blood normally pumped upon contraction of such ventricles. More specifically, a left ventricular assist device (LVAD) helps to pump oxygenated blood to the aorta or associated arteries. The following description is directed more particularly to examples of LVADs, although various acts and apparatus described herein will find use in other devices, systems and methods.

Figure 2:
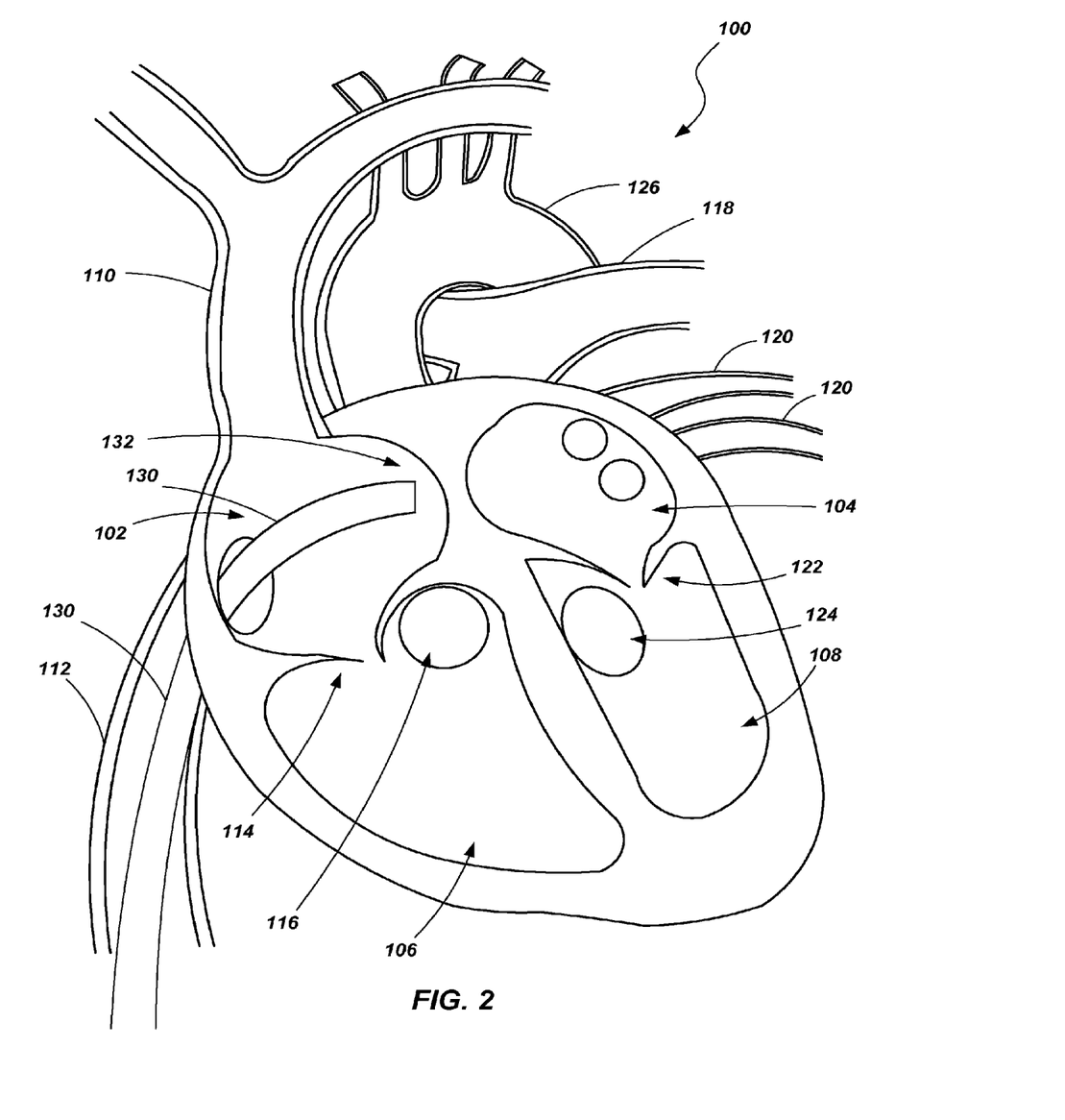
FIGS. 2 through 11 are simplified, cross-sectional views of a human heart at different stages of a procedure according to embodiments of the present invention and utilizing various devices and components in accordance with certain embodiments of the present invention.

Referring to FIG. 2, a catheter 130 is directed to the right atrium 102 through the inferior vena cava 112, such as by a femoral vein. The catheter 130 may be guided using the assistance of fluoroscopic imaging, ultrasound imaging or both. Such access of the right atrium 102 via a femoral vein is well known to those of ordinary skill in the art and is not described in further detail herein. The catheter 130 may be used to perform a procedure such as puncturing the septum 132 separating the right atrium 102 from the left atrium 104. By puncturing the septum 132 access to oxygenated blood may be obtained through the right atrium 102.

Figure 3:
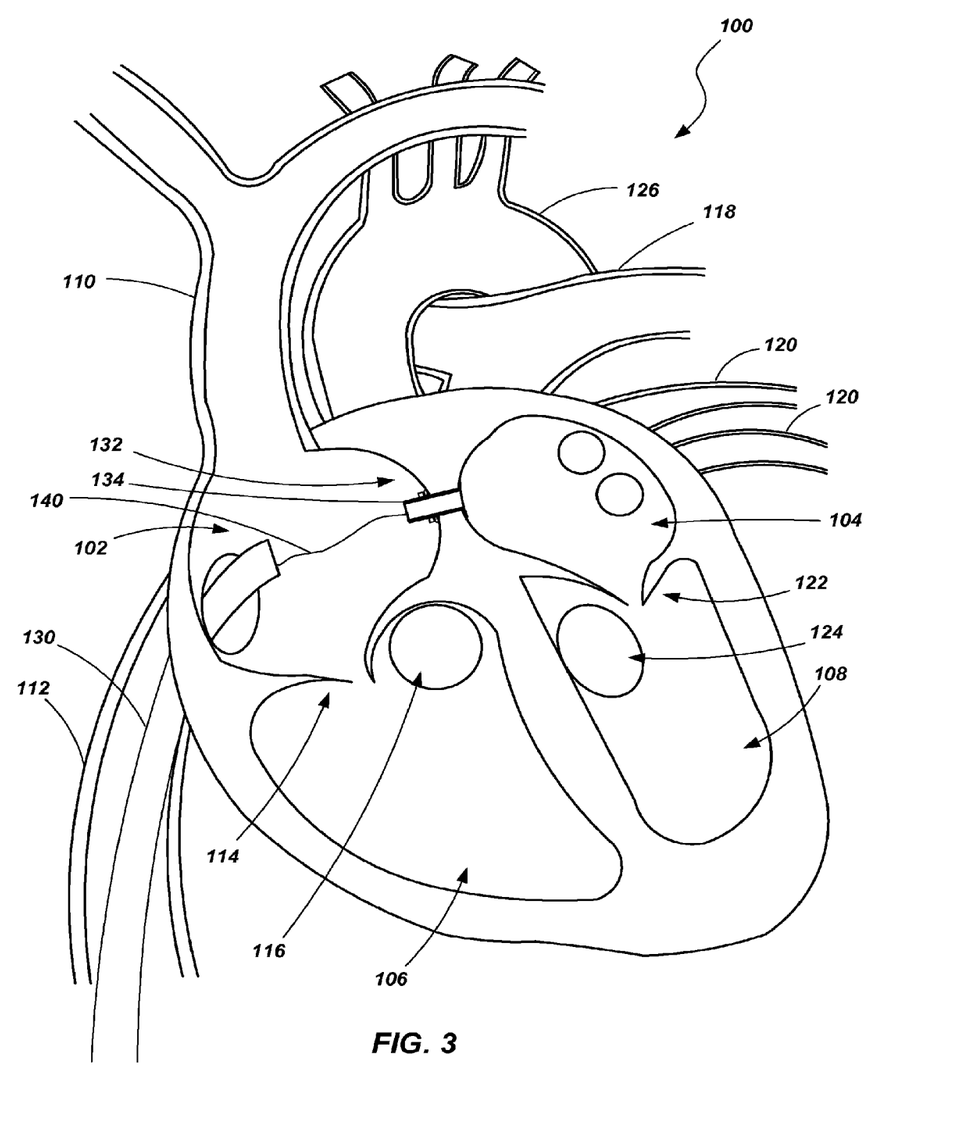
Figure 12:
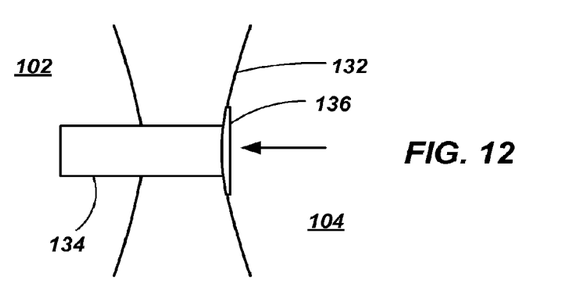
FIG. 12 is a component utilized in association with a ventricular assist device in accordance with an embodiment of the present invention.

As shown in FIG. 3, an anastomosis device 134 may be inserted through and coupled to the septum 132. In one embodiment, the anastomosis device 134 may be configured such that it extends into the right atrium 102 but does not substantially extend into the left atrium 104. For example, as seen in FIG. 12, the anastomosis device 134 may have a small shoulder 136 or other feature or structure that abuts the left atrial side of the septum 132 to create a relatively smooth or flush transition along the septum all and into a passage or flow channel defined by the anastomosis device 134. By keeping the anastomosis device 134 substantially out of the left atrium 104, and by having a smooth transition from the septum wall into the passage of the anastomosis device 134, the potential of thrombosis formation is reduced, the amount of pressure required to draw oxygenated blood from the left atrium 104 is also reduced and there is less likelihood of hemolysis (red blood cell damage).

Figure 13:
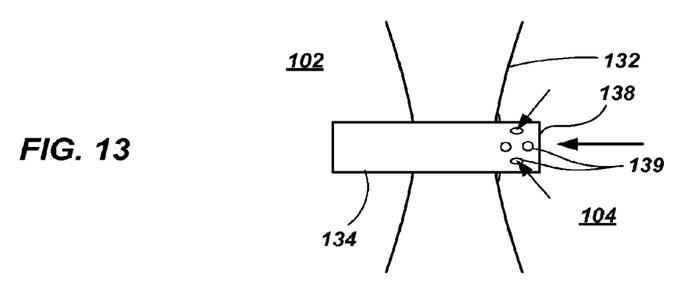
FIG. 13 is a component utilized in association with a ventricular assist device in accordance with another embodiment of the present invention.
Figure 14:
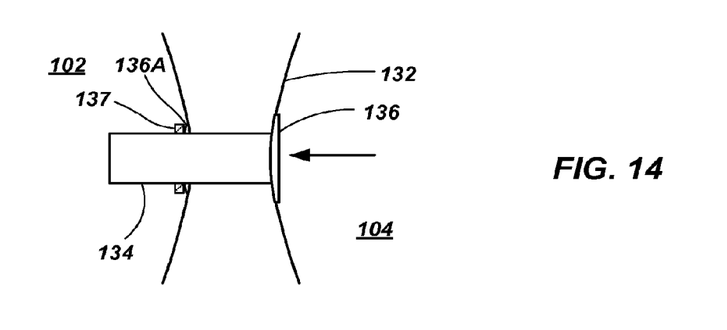
FIG. 14 is a component utilized hi association with a ventricular assist device in accordance with an embodiment of the present invention.

It is noted, briefly, that other configurations of an anastomosis device 134 may be utilized. For example, it is contemplated that a portion of the anastomosis device 134 may protrude into the left atrium such as shown in FIG. 13. In such a case, an opening on the end 138, as well as lateral openings 139 may he used to draw blood from the left atrium 104. Again, such a structure enables blood to be drawn from the left atrium 104 with a relatively reduced level of pressure as compared to what is known as a reentrant connection where, for example, the end of the device protrudes into the left atrium and blood is drawn only through the opening at the end 138. As shown in FIG. 14, coupling of the anastomosis device may include positioning a grommet or a biasing member 137 (such as a member made of foam, elastomer, or other resilient material) against a shoulder 136A positioned on the right atrial side of the septum 132, the biasing member 137 may be used to effect a tighter fit of the anastomosis device 134 within the septum 132.

In one embodiment, the anastomosis device grommet 137 may be configured of a porous material to promote tissue in-growth and more securely connect the anastomosis device 134 to the septal tissue. Such materials might include, for example, foam, sintered titanium, porous tantalum, porous polytetrafluoroethylene (PTFE) or other porous material.

Figure 4:
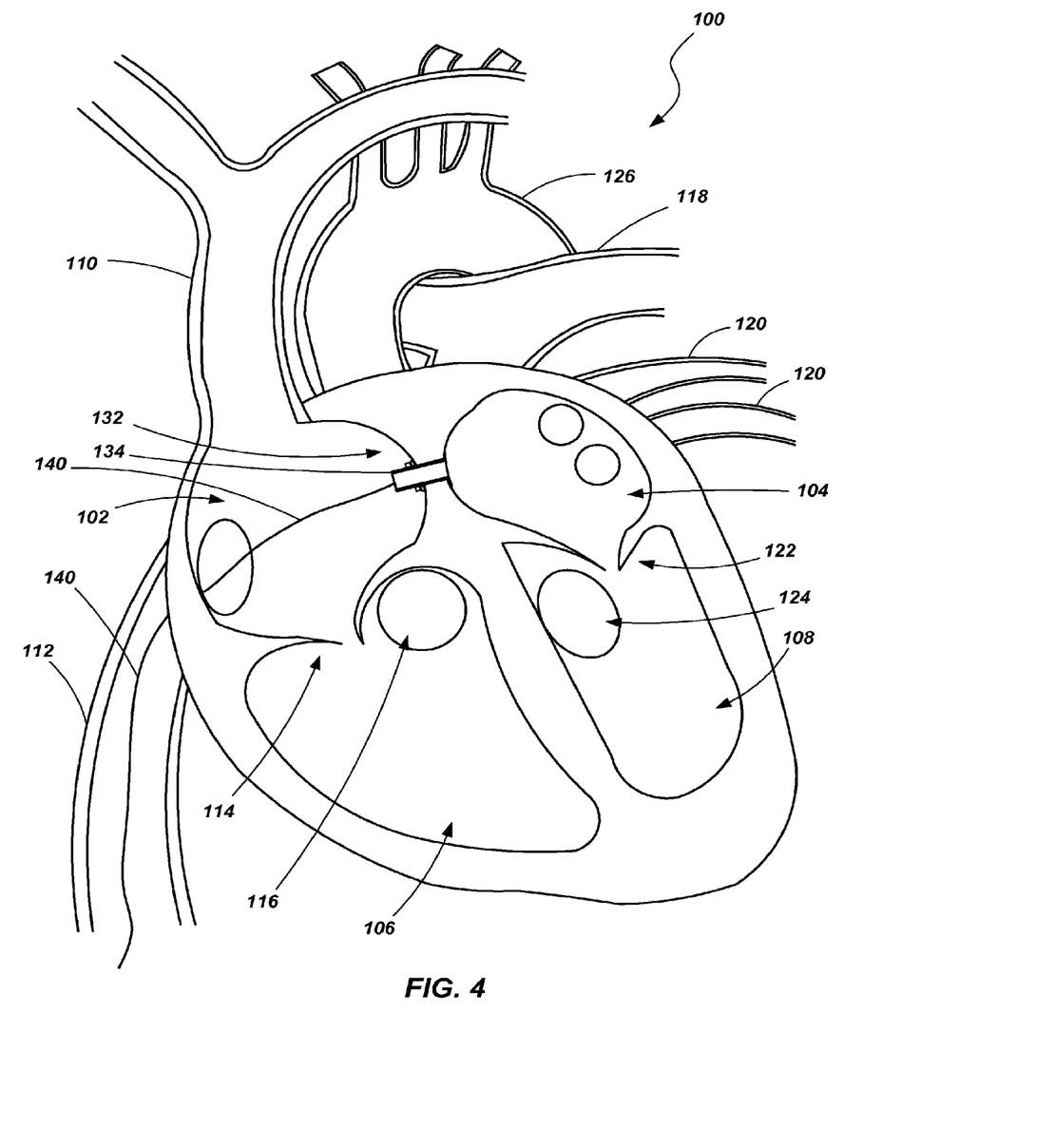

Referring to both FIGS. 3 and 4, as the catheter 130 is withdrawn, a filament member 140 remains with an end attached to the anastomosis deice 134. The filament member 140 may include, for example, a strand of fibrous material, a braided member, a polymeric material a suturing material, or even a slender flexible wire. The filament member 140 may also be formed of a material, or include markers formed therein, that is (are) detectable by various imaging techniques to verify its position within the heart and veins. Examples of materials that may be used to form the filament that provide radio opacity include, but are not limited to, a wire made from tantalum, tantalum-tungsten alloy, platinum, platinum-iridium and stainless steel. Additionally, a wire may be coated with a polymer (e.g., nylon, urethane, PTFE, expanded PTFE or some polymer). When the catheter 130 is withdrawn, the filament member 140 remains attached to the anastomosis device 134 and may have a portion extending through the inferior vena cava 112 and, possibly, through other veins. In one embodiment, the filament may extend all the way through the access point, such as through an access point for a femoral vein.

Figure 5:
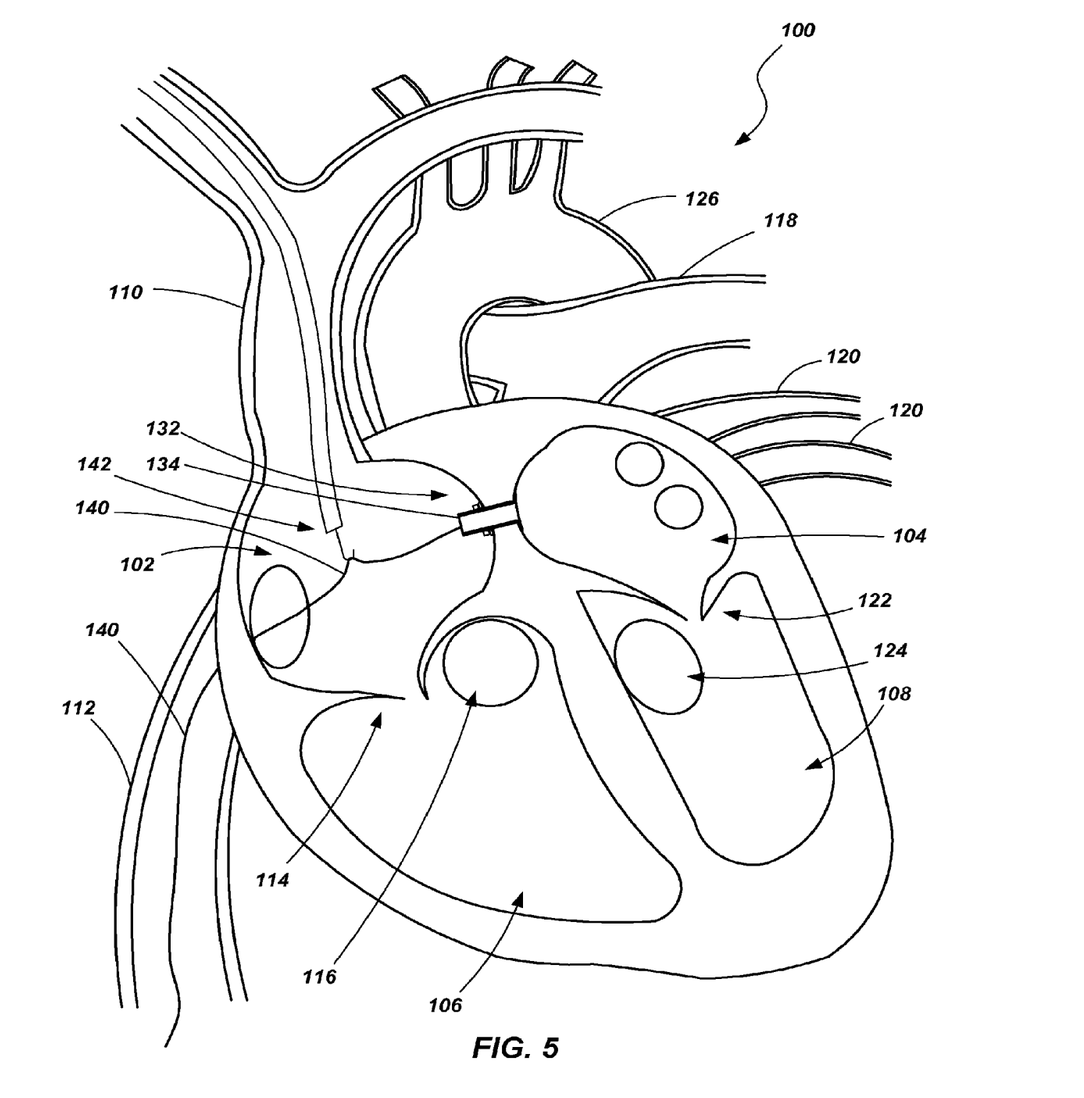
Figure 6:
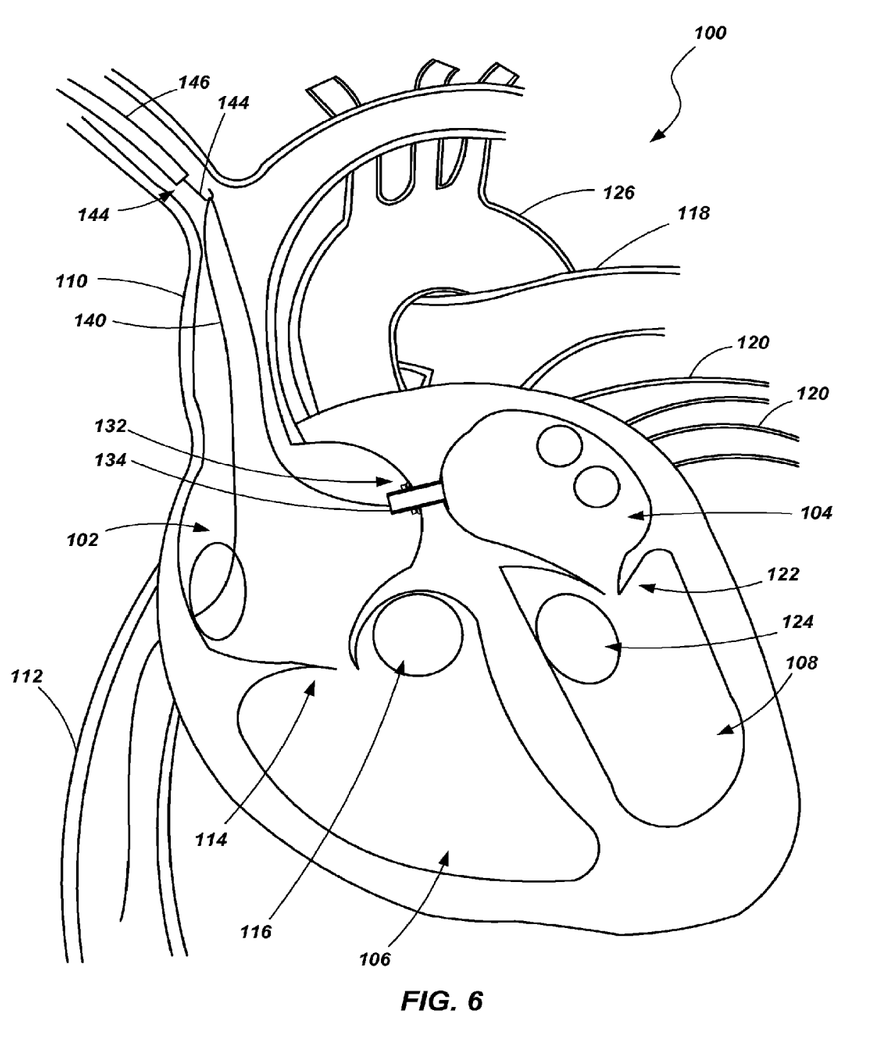
Figure 7:
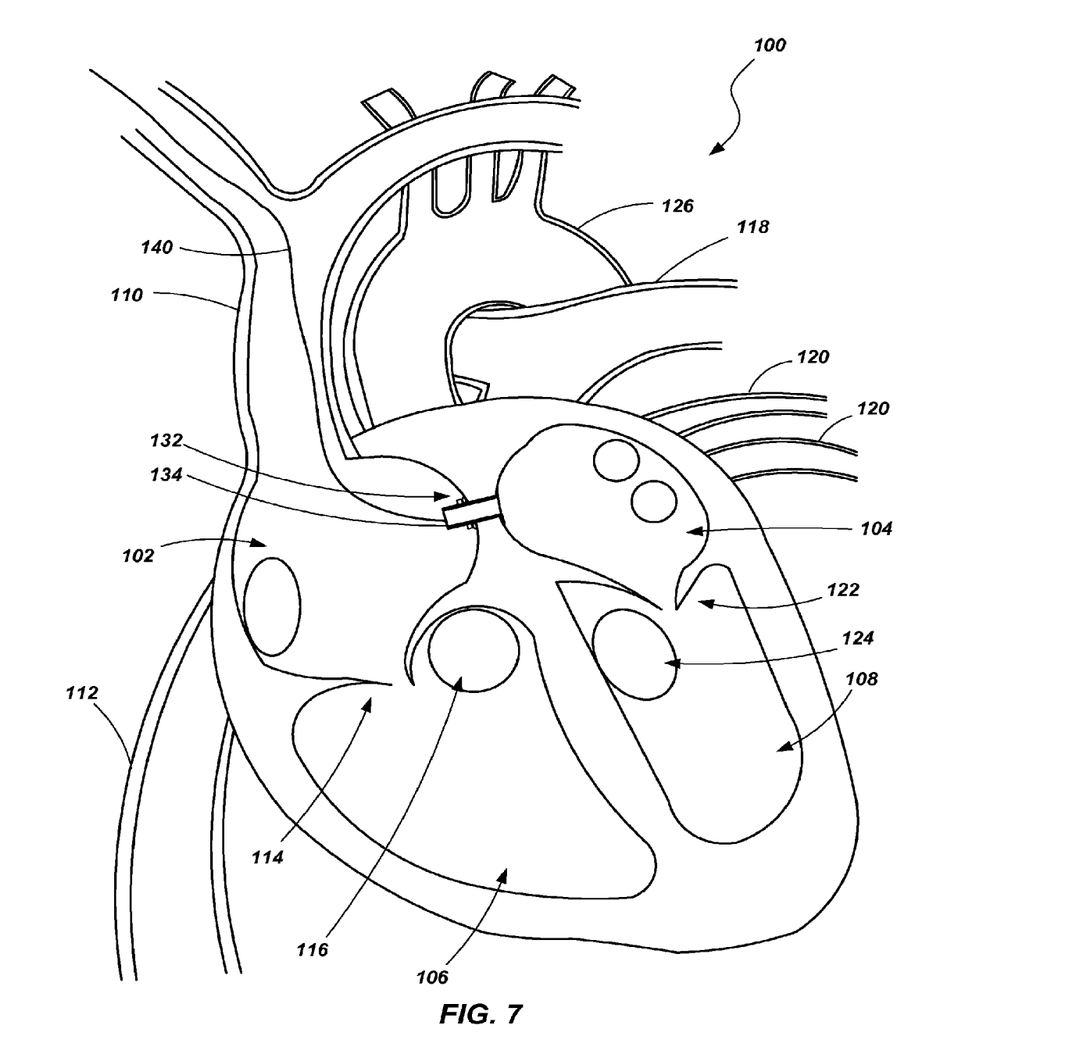

Referring to FIG. 5, a snare device 142 may be introduced into the right atrium 102 through the superior vena cava 110, such as by way of a jugular vein or the subclavian vein. The snare device 142 may be used to snare or grasp a portion of the filament member 140 disposed within the right atrium 102. Once the snare device 142 has grasped a portion of the filament member 140, the snare device 142 maybe withdrawn from the right atrium 102 and then back through the superior vena cava 110. While not specifically shown, it is noted that the tip 144 of the snare device 140 may be positionable relative to an associated catheter housing 146 such that, while the snare device 140 is being deployed and withdrawn, it does not damage the tissue of the heart or veins to which the snare device 140 is exposed. As shown in FIGS. 6 and 7, as the snare device 142 is withdrawn, the filament member 140 is pulled up through the superior vena cava 110 and through any other vein (e.g., the jugular vein or the subelavian vein) which was used by the snare device 142 in gaining access to the right atrium 102.

Figure 8:
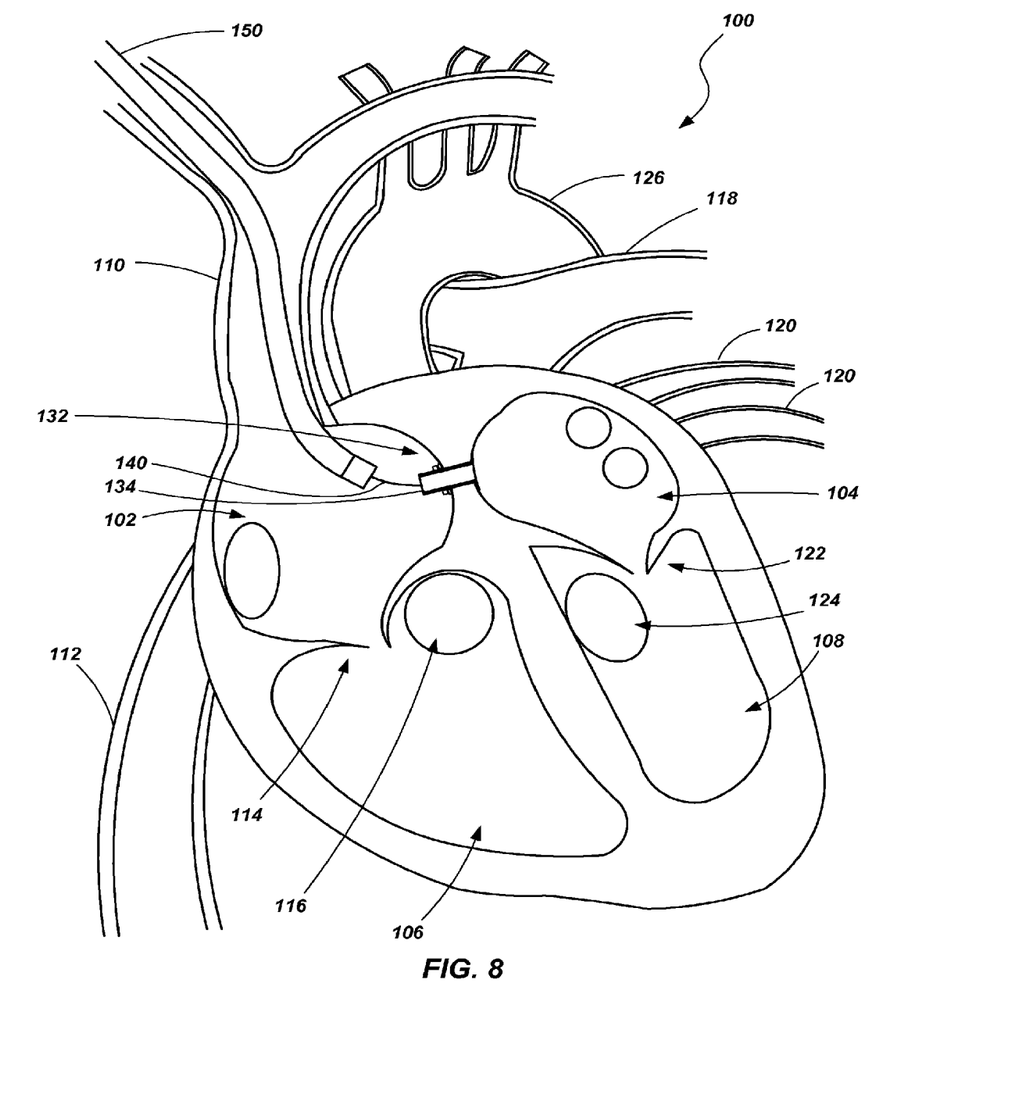
Figure 9:
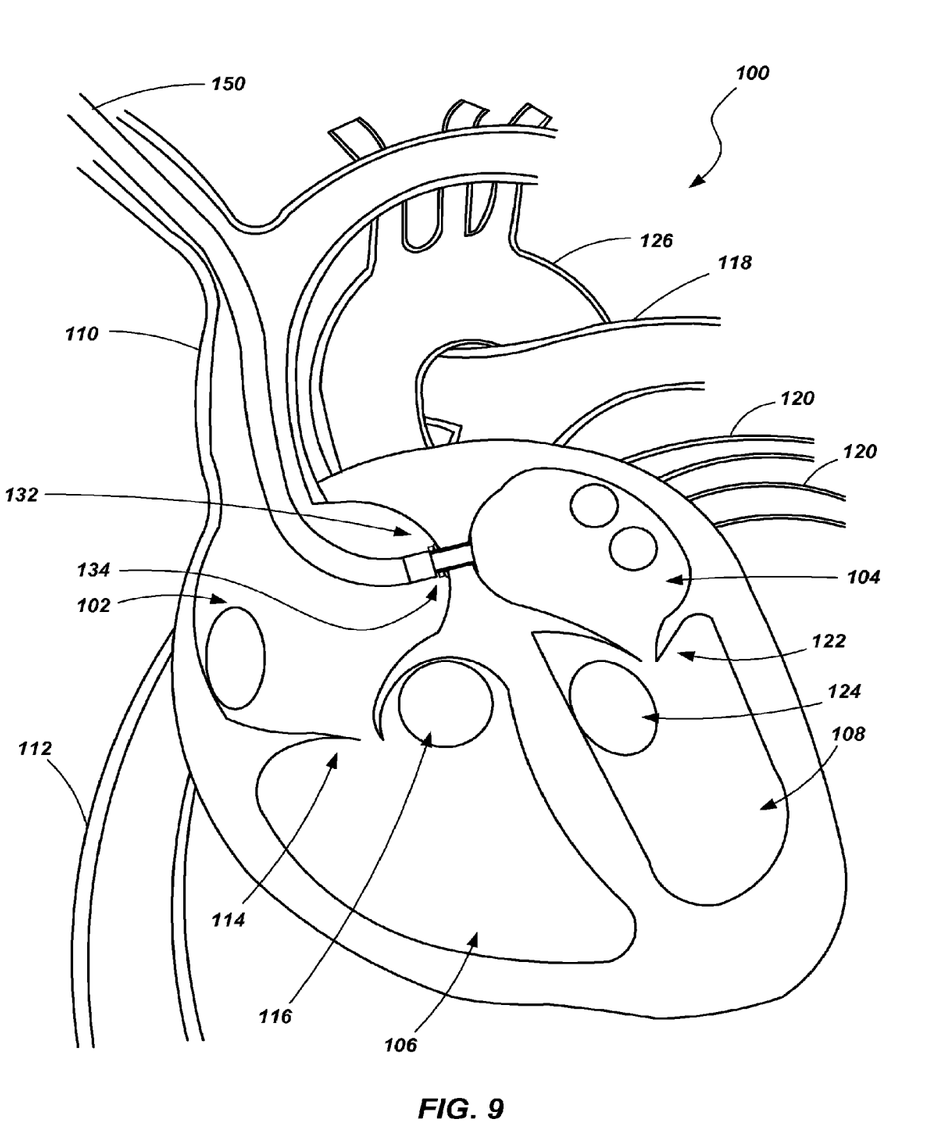

Referring to FIG. 8, a conduit 150 may be inserted into the right atrium 102, using the filament member 140 as a guide to follow the same path that was used by the snare device 142. FIG. 9 shows the conduit 150 coupled with the anastomosis device 134 creating a flow path for oxygenated blood from the left atrium 104, through the right atrium 102 (via the anastomosis device 134), through the superior vena cava 110 and through another vein such as the jugular or subclavian vein. The conduit 150 may include appropriately sized tubing or other material configured to be compatible with human tissue and to provide a fluid flow path for oxygenated blood from the left atrium 104 of the heart 100.

Figure 10:
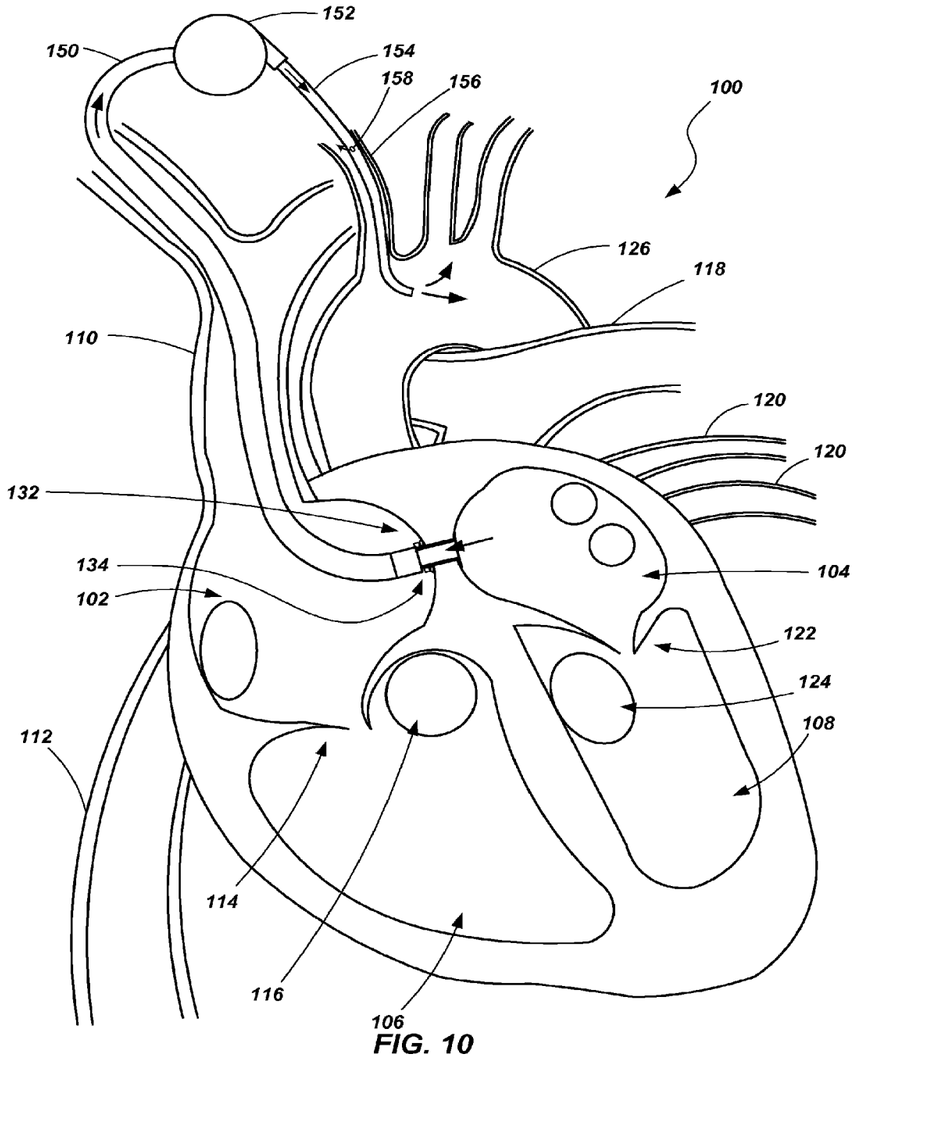

Referring to FIG. 10, the conduit 150 is coupled to a pumping device 152 which, in one embodiment, may be located external to the patient's body. A return conduit 154 is also coupled with the pumping device 152. The return conduit 154 is inserted into an artery to return the oxygenated blood to the circulatory system. For example, an outlet end of the return conduit 154 may be disposed in the aorta 126. The return conduit 154 may be routed, for example, through a brachial artery 156, although other appropriate routes may be utilized including a carotid artery. For example, the return conduit 154 may be routed to return flow to the left subclavian artery. In another embodiment, the return conduit 154 be routed through the left subclavian artery and into the aortic arch, directing flow of blood downstream to prevent possible thrombi from entering, for example, the brachiocephalic artery or the left common carotid artery and traveling to the brain.

It is noted that, in some instances when the return conduit 154 is of a size that may obstruct or otherwise limit the flow of blood through the artery in which it is disposed (e.g., the brachial artery 156), one or more openings 158 may be formed within the return conduit 154 at upstream locations so that blood flow may be maintained within the associated artery hosting the return conduit 154.

In one example, the pumping device 152 may include a pump similar to a pump offered by Cardiac Assist, Inc. under the mark of TandemHeart®. The TandemHeart® pump is capable of pumping up to 5.0 liters per minute (lpm) when used percutaneously such as with the presently described system.

Figure 11:
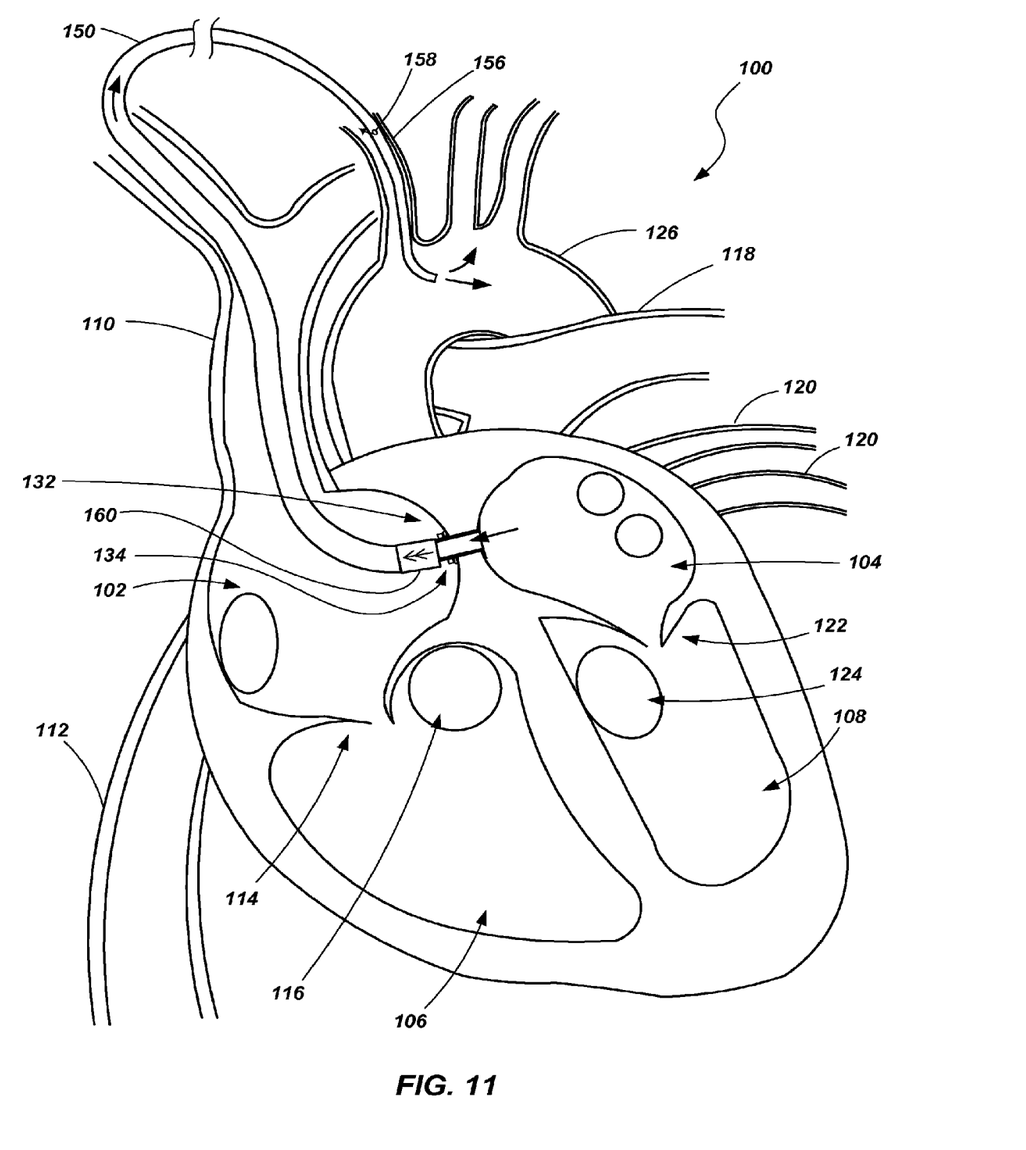

Referring briefly to FIG. 11, in another embodiment, the conduit 150 may extend from the right atrium 102 until it is returned into the aorta 126, such as through a brachial artery 156 or other route. A pumping device 160 is located within the right atrium 102 and coupled between the anastomosis device 134 and the conduit 150 effectively placing the pumping action at the septum 132. By locating pump at the septum 132, the oxygenated blood is subjected to less of a "vacuum" force and less head may be required. in other embodiments, the pumping device 160 may be located in the left atrium 104, the right ventricle 106 or the left ventricle 108. In such a case, wires or other transmission lines may also be feed through the superior vena cava 110 into the heart 100 to provide power to, and control of, the pumping device 160. In one embodiment, such wires may extend along side the conduit 150. In another embodiment, the wires may extend through a separate and distinct lumen formed within the conduit 150 or be contained within the wall of the conduit 150.

One example of a pump that may be placed in the right atrium (or even in on of the veins leading to the right atrium 102) is the pump utilized by Abiomed, Inc. with the product offered under the trademark Impella™. Of course, other suitable pumps, such as the above described TandemHeart® pump, may also be utilized.

In either of the embodiments shown in FIG. 10 or 11, oxygenated blood is drawn from the left atrium 104, through the anastomosis device 134, through the conduit 150 which passes through the superior vena cava and other veins such as the jug Jar or the subclavian, and is then returned to the aorta 126 through the return conduit 154 (or via the conduit itself in FIG. 11) which passes through an artery such as a brachial artery or a carotid artery.

One advantage of the described systems and methods includes the placement of the conduits. By routing the conduits (e.g., 150 and 154) through the superior vena cava 110 and arteries such as a brachial artery or a carotid artery, the system is easier to maintain and infections are less likely to occur. Often, when conduits are routed through the femoral veins or arteries for ventricular assist devices, infection is a likely complication. Additionally, use of a filament to guide the conduit 150 to the septum 134 is advantageous as it is difficult to steer and access a structure to such a location via the superior vena cava independent of such a guide structure.

Figure 15:
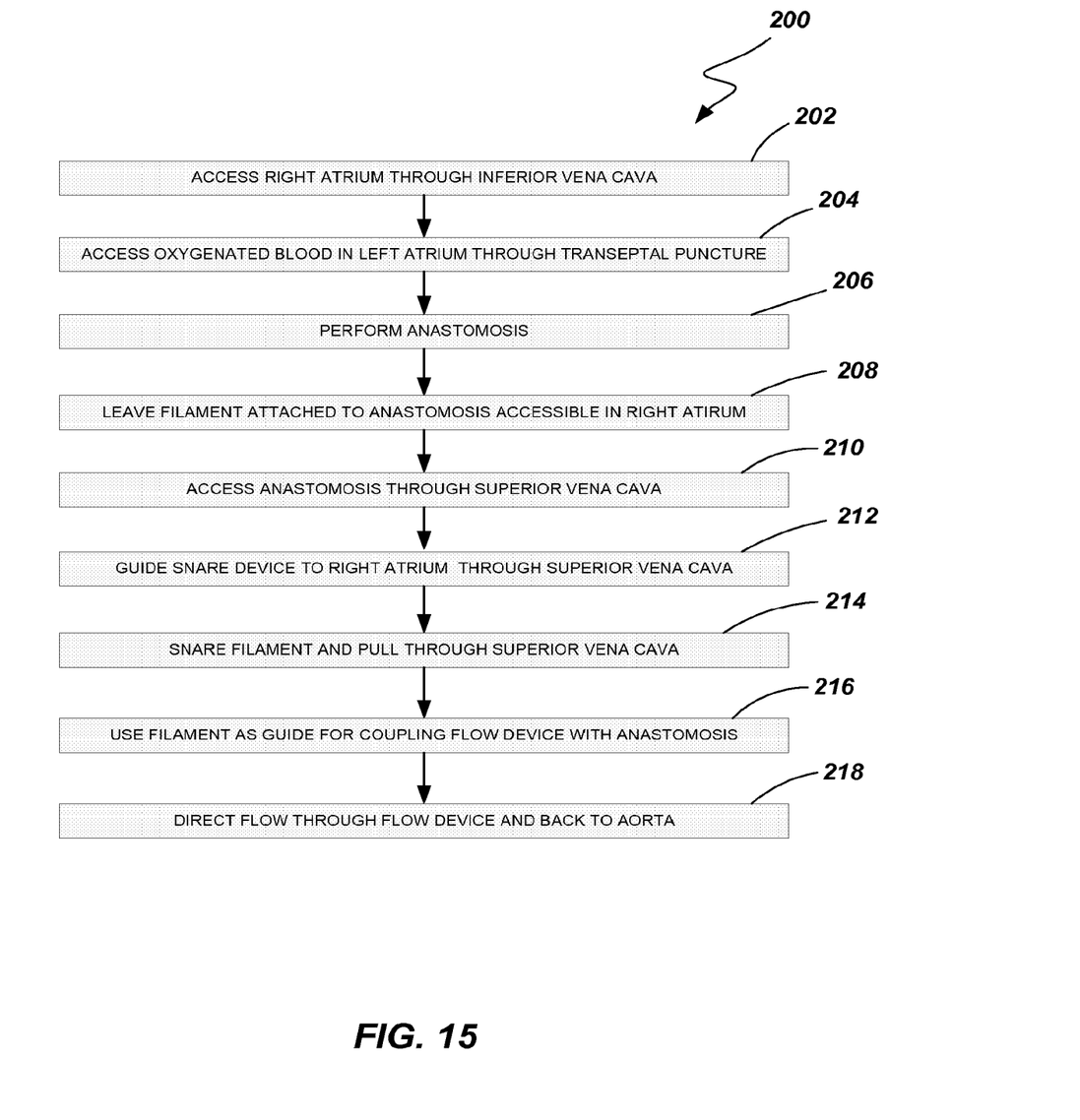
FIG. 15 is a block diagram showing various acts in one example of percutaneously gaining access to oxygenated blood and pumping such blood to other arterial regions of the vascular system via an LVAD, according to an embodiment of the present invention.

Referring no to FIG. 15, various acts of a method 200 according to the present invention are shown. As described above with respect to FIGS. 2-11, the method provides access to oxygenated blood with an anastomosis device and includes pumping such oxygenated blood to other arterial regions of the vascular system. Such access to oxygenated blood is first initiated by percutaneous access to the femoral vein. As depicted at 202, a catheter may be inserted through the femoral access point up through the inferior vena cava into the right atrium. As previously noted, the catheter may be guided with the assistance of for example, fluoroscopic and/or ultrasound imaging. As depicted at 204, a trans-septal puncture may be performed at a location in the atrial septum accessing oxygenated blood contained in the left atrium. As shown at 206, anastomosis can be performed with a catheter-based device which, in one embodiment, attaches only to the right atrial side of the atrial septum preventing potential thrombus formation or securement issues of an cannula protruding through the septal wall, or into the left atrium. Further, by attaching an anastomosis device to the right atrial side of the atrial septum, there is far less resistance to flow of the blood from the left atrium than that of an in-flow cannula protruding through the septal wall and into the left atrium.

As set forth at 208, after the anastomosis is performed, the catheter system can be withdrawn from the right atrium, from which a filament remains connected to the anastomosis device. As shown at 210, the anastomosis device is accessed by percutaneous access through the venous system, such as the subclavian or jugular vein. An intra-vascular snare device can be inserted through this subclavian or jugular vein access point and guided into the right atrium, as set forth at 212. The snare device can then be used to snare the filament that is attached to the anastomosis device and to exteriorize it through the access point, as set forth at 214.

As set forth at 216, the filament can then be used as a guide to insert a conduit, such as the in-flow catheter of a VAD pump, through the access point and up to the anastomosis device where it is attached thus providing access to oxygenated blood to the VAD pump. As set forth at 218, a conduit, such as an out-flow catheter of the pump, is percutaneously attached to a brachial artery or a carotid artery or even the aorta via another anastomosis device or another type of connection. In one embodiment, this additional anastomosis device can be similar to that used for connection of the in-flow catheter to the atrial septum. Further, it is contemplated that the LVAD can be disposed externally or internally, In one embodiment, the LVAD can be disposed in the chest, external the ribs or thoracic cavity, in the soft tissue, similar to a pace-maker.

Having considered the above examples, it is further noted that a similar procedure may be performed in the ventricles 106 and 108 of the heart 100 rather than the atria 102 and 104. For example, access to the right ventricle 106 may be obtained by first accessing the right atrium 102, as described above, and then passing a catheter 130 or other device through the tricuspid valve 114 into the right ventricle 106. The septum between the right and left ventricles 106 and 108 may then be punctured to access oxygenated blood in the left ventricle 108. An anastomosis device 134 may then be positioned in the septum between the right and left ventricles and the procedure may follow as outlined above, except that access to oxygenated blood will be through the anastomosis device in the right ventricle 106 rather than in the right atrium 102.

Additionally, while the description above has been set forth as performing, the anastomosis procedure by access through the inferior vena cava 112, it is noted that access to the right atrium 102 or right ventricle via the inferior vena cava 112 may simply be to attach a filament 140 to, for example, the septum (either between atria 102 and 104 or between ventricles 106 and 108). The filament 140 may then be used to guide a conduit or other cannula to the septum, the conduit or cannula having an anastomosis device to be installed in the septum.

It is further noted that various acts or portions of the described embodiment may be used independent of others. Thus, the present invention contemplates transeptal access to the left side of the heart for use in other procedures, or in procedures where the oxygenated blood is routed differently than described in the example embodiments set forth above.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A method of guiding a structure to a right atrium or right ventricle of a heart, the method comprising:
   accessing one of the right atrium and the right ventricle through an inferior vena cava;
   attaching a filament to one of a wail of the right atrium and the right ventricle;
   accessing the heart through the superior vena cava;
   grasping the filament with a snare device and withdrawing the snare device and filament through the superior vena cava; and
   guiding the structure through the superior vena cava into one of the right atrium and the right ventricle using the filament.

2. The method according to claim 1, wherein attaching a filament includes placing an anastomosis device through a septum, the anastomosis device having the filament attached thereto.

3. The method according to claim 2, wherein accessing the heart through the superior vena cava further includes accessing the superior vena cava through at least one of a jugular vein and a subciavian vein.

4. The method according to claim 3, wherein guiding the structure through the superior vena cava into one of the right atrium and the right ventricle using the filament further includes guiding a conduit into one of the right atrium and the right ventricle and coupling the conduit with the anastomosis device.

5. The method according to claim 1, further comprising placing an anastomosis device through a septum subsequent to guiding the structure through the superior vena cava into one of the right atrium and the right ventricle using the filament.

6. A method of guiding a structure to a right atrium or right ventricle of a heart, the method comprising:
   accessing one of the right atrium and the right ventricle through an inferior vena cava;
   attaching a filament to as wall of one of the right atrium and the right ventricle;
   accessing the heart through the superior vena cava with a snare device;
   pulling the filament with the snare device and withdrawing the snare device and filament through the superior vena cava; and
   guiding the structure through the superior vena cava into one of the right atrium and the right ventricle using the filament.

7. The method according to claim 6, wherein attaching a filament comprises attaching an anastomosis device in the wall, the anastomosis device having the filament attached thereto.

8. The method according to claim 6, wherein accessing the heart through the superior vena cava further includes accessing the superior vena cava through at least one of a jugular vein and a subclavian vein.

9. The method according to claim 6, wherein guiding the structure through the superior vena cava into one of the right atrium and the tight ventricle using the filament further includes guiding a conduit into one of the right atrium and the right ventricle and coupling the conduit with the anastomosis device.

10. The method according to claim 6, further comprising placing an anastomosis device in the wall subsequent to guiding the structure through the superior vena cava into one of the right atrium and the right ventricle using the filament.

11. The method according to claim 7, wherein guiding the structure comprises guiding a conduit to the anastomosis device and coupling the conduit to the anastomosis device.

12. The method according to claim 11, further comprising flowing oxygenated blood from one of the left atrium and the left ventricle through the conduit via a pumping device.

13. The method according to claim 12, further comprising returning the oxygenated blood from the conduit to an artery.

14. The method according to clam 12, wherein flowing oxygenated blood comprises flowing the oxygenated blood with the pumping device positioned in a flow path of the oxygenated blood between the superior vena cava and the aorta.

15. The method according to claim 12, wherein flowing oxygenated blood comprises flowing the oxygenated blood with the pumping device positioned within at least one of the right atriumn, the left atrium, the right ventricle, and the left ventricle of the heart.

16. The method according to claim 6, wherein the pulling the filament comprises snaring the filament with the snare device.

* * * * *